United States Patent
Kolb et al.

(10) Patent No.: US 6,642,390 B2
(45) Date of Patent: Nov. 4, 2003

(54) ONE STEP SYNTHESIS OF 1,2,3-TRIAZOLE CARBOXYLIC ACIDS

(75) Inventors: Hartmuth C. Kolb, East Windsor, NJ (US); Cullen Cavallaro, Lawrenceville, NJ (US); Zhi-Cai Shi, North Brunswick, NJ (US); Alexander Gontcharov, Kendall Park, NJ (US); Zhi-Min Wang, North Brunswick, NJ (US); Paul F. Richardson, Monmouth Junction, NJ (US); Ramanaiah C. Kanamarlapudi, Bridgewater, NJ (US)

(73) Assignee: Lexicon Pharmaceuticals, Inc., New Brunswick, NJ (US)

( * ) Notice: Subject to any disclaimer, the term of this patent is extended or adjusted under 35 U.S.C. 154(b) by 0 days.

(21) Appl. No.: 10/193,591

(22) Filed: Jul. 11, 2002

(65) Prior Publication Data

US 2003/0135050 A1 Jul. 17, 2003

Related U.S. Application Data

(60) Provisional application No. 60/304,462, filed on Jul. 11, 2001.

(51) Int. Cl.$^7$ ............ C07D 249/04; C07D 249/06
(52) U.S. Cl. ............................................. 548/255
(58) Field of Search .................................. 548/255

(56) References Cited

PUBLICATIONS

Hirota et al., "Synthesis and Anti–human Immunodeficiency Virus (HIV–1) Activity of 3'–Deoxy– 3'–(triazol–1–yl)thymidines and 2',3'–Dideoxy–3'–(triazol–1–yl)uridines, and Inhibition of Reverse Transcriptase by Their 5'–Triphosphates," *Chem Pharm. Bull.* 38(9):2597–2601 (1990).

Palacios et al., "Synthesis of Diethyl 1,2,3–Triazolealkyl–Phosphonates Through 1,3–Dipolar Cycloaddition of Azides With Acetylenes," *Heterocycles* 38(1):95–102 (1994).

Bertelli et al., "1,2,3–Triazolo[1,5–a]quinoxalines: synthesis and binding to benzodiazepine and adenosine receptors," *Eur. J. Med. Chem.* 33(2):113–122 (1998).

Lindsay et al., *Org. Synth. Coll.* vol. 3, pp. 710–711. (Date unknown).

Alvarez et al., "A Practical Procedure for the Synthesis of Alkyl Azides at Ambient Temperature in Dimethyl Sulfoxide in High Purity and Yield," *Synthesis*, pp. 413–414 (Apr. 1997).

Oikawa et al., *Org. Synth. Coll.* vol. 7, pp. 359–361 (1988).

Oikawa et al., "Meldrum's Acid in Organic Synthesis. 2 A General and Versatile Synthesis of ss–Keto Esters," *J. Org. Chem.*, 43(10):2087–2088 (1978).

Capozzi et al., "A Protocol for the Efficient Synthesis of Enantiopure ss–Substituted ss–Lactones," *J. Org. Chem.*, 58:7932–7936 (1993).

*Primary Examiner*—Patricia L. Morris
(74) *Attorney, Agent, or Firm*—McDonnell Boehnen Hulbert & Hulbert

(57) ABSTRACT

Disclosed is a one step method for preparing a 1,2,3-triazole carboxylic acid by treating an azide with a β-ketoester in the presence of a base.

13 Claims, No Drawings

ONE STEP SYNTHESIS OF 1,2,3-TRIAZOLE CARBOXYLIC ACIDS

This application claims the benefit of U.S. Provisional Patent Application No. 60/304,462, filed Jul. 11, 2001.

BACKGROUND OF THE INVENTION

1. Field of the Invention

This invention relates to a one-step process to prepare triazole carboxylic acids from azides and β-ketoesters.

2. Description of the Related Art

The 1,2,3-triazole unit is an important element in a number of drugs and development candidates. The triazole is a structural backbone of many antibiotics, antiallergics, antimetastasis agents, anticonvulsants and antidepressants. Their synthesis usually involves the reaction of organic azides with unsaturated compounds. Such unsaturated compounds are usually acetylenic compounds (Hiroto et al., *Chem Pharm. Bull.* 1990, 38(9), 2597–2601; Palacios et al., *Heterocycles* 1994, 38(1), 95–102), as, for example, acetylene dicarboxylic acid derivatives. Because these acetylenic starting materials usually carry the same substituents on both acetylenic carbon atoms, the reaction gives rise to symmetrically substituted 1,2,3-triazoles (i.e. 1,2,3-triazoles carrying identical substituents in positions 4 and 5). If unsymmetrical substituted acetylenes are used, the resulting 1,2,3-triazoles are usually mixtures of regioisomers. Regioselectivity issues can be avoided with β-ketoesters as starting materials (Bertelli et al., *Eur. J. Med. Chem.* 1998, 33(2), 113–122). However, β-ketoesters have been used only in rare cases, and the yields have been poor. Additionally, azides are difficult to obtain, and published 1,2,3-triazole syntheses are usually not very efficient with respect to throughput and scale.

An object of the present invention is to develop a large scale, safe and efficient procedure for the syntheses of azides. Another object of the present invention is to provide an efficient one-step synthesis of triazole-carboxylic acids from azides and β-keto esters.

SUMMARY OF THE INVENTION

This invention provides for a one step process for preparing 1,2,3-triazole carboxylic acids from an azide and a β-ketoester. Specifically, the method of the present invention calls for the treatment of an azide and a β-ketoester with a base to form a 3H-[1,2,3]triazole-4-carboxylic acid. These compounds are important precursors for antibiotics, antiallergics, antimetastasis agents, anticonvulsants and antidepressants.

The invention also provides for a method for preparing an aromatic azide intermediate from an aromatic amine. The aromatic amine is treated with a nitrate ion in the presence of an acid to form a diazonium salt. Subsequent treatment with an azide ion affords the desired aromatic azide.

The invention further provides for a method for preparing an aliphatic azide intermediate from the corresponding alkyl halide and an azide ion. The reaction proceeds via $S_N2$ nucleophilic aliphatic substitution and the time and temperature of the reaction is dependent on the individual alkyl halide.

The invention further provides for a method for preparing a β-hydroxy aliphatic azide intermediate by regioselective nucleophilic opening of an epoxide by an azide ion in the presence of ammonium chloride. For azides to be converted to the corresponding 1,2,3-triazole carboxylic acids according to the method of the present invention, the alcohol is subsequently protected.

DETAILED DESCRIPTION OF THE INVENTION

According to Scheme 1, a preferred embodiment of the present invention relates to a method for the formation of a 3H-[1,2,3]triazole-4-carboxylic acid III by reacting an azide I with a β-ketoester II in the presence of a base.

Scheme 1

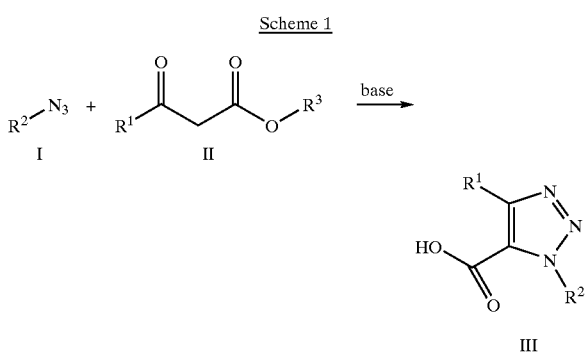

In Scheme 1:

$R^1$ and $R^2$ independently are lower alkyl or cycloalkyl optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, —NHC(O)-alkyl, alkenyl or alkynyl, or $R^1$ and $R^2$ independently are aryl, arylalkyl, cycloalkylalkyl, heteroaryl or heteroarylalkyl wherein the ring portion of each is optionally substituted with one, two or three groups independently selected from halogen, lower alkoxy, —C(O)-alkyl, hydroxy, amino, mono- or dialkylamino, mercapto, alkylthiol, —C(O) NH-alkyl, C(O)N-dialkyl, —NHC(O)-alkyl, alkenyl or alkynyl; and $R^3$ is lower alkyl.

In a more preferred embodiment of the invention $R^2$ is aryl or heteroaryl optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O) N-dialkyl, —NHC(O)-alkyl, alkenyl or alkynyl.

By "alkyl", "lower alkyl", and "$C_1$–$C_6$ alkyl" in the present invention is meant straight or branched chain alkyl groups having 1–6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. These groups may be substituted with up to four groups mentioned below for substituted aryl.

By "alkoxy", "lower alkoxy", and "$C_1$–$C_6$ alkoxy" in the present invention is meant straight or branched chain alkoxy groups having 1–6 carbon atoms, such as, for example, methoxy, ethoxy, propoxy, isopropoxy, n-butoxy, sec-butoxy, tert-butoxy, pentoxy, 2-pentyl, isopentoxy, neopentoxy, hexoxy, 2-hexoxy, 3-hexoxy, and 3-methylpentoxy. These groups may be substituted with up to four groups mentioned below for substituted aryl.

By the term "halogen" in the present invention is meant fluorine, bromine, chlorine, and iodine.

A "carbocyclic group" or "cycloalkyl" is a nonaromatic cyclic ring or fused rings having from 3 to 7 ring members. Examples include cyclopropyl, cyclobutyl, and cycloheptyl. These rings may be substituted with one or more of the substituent groups mentioned below for aryl, for example alkyl, halo, amino, hydroxy, and alkoxy. Typical substituted carbocyclic groups include 2-chlorocyclopropyl, 2,3-diethoxycyclopentyl, and 2,2,4,4-tetrafluorocyclohexyl. The carbocyclic group may contain one or two heteroatoms selected from oxygen, sulfur, and nitrogen, and such ring systems may be referred to as "heterocyclyl" or "heterocyclic". Examples include pyranyl, tetrahydrofuranyl, and dioxanyl. These heterocyclyl groups may be substituted with up to four of the substituent groups mentioned for aryl.

By heteroaryl is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, imidazolyl, (is)oxazolyl, pyridyl, pyrimidinyl, (iso)quinolinyl, napthyridinyl, benzimidazolyl, benzoxazolyl. The heteroaryl group is optionally substituted with up to four groups mentioned below for substituted aryl.

By aryl is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which is optionally mono-, di-, or trisubstituted with, e.g., halogen, —OH, —SH, lower alkyl, lower alkoxy, lower alkylthio, trifluoromethyl, trifluoromethoxy, lower acyloxy, aryl, heteroaryl, amino, mono- or dialkylamino, and nitro. A preferred aryl is phenyl.

In another more preferred embodiment, the azide I, the β-ketoester II and the base are reacted together in a suitable solvent. The reaction mixture in such a solvent can be homogenous or heterogenous. Examples of suitable solvents for the present method include, but are not limited to, one or more of the following: a protic solvent such as methanol, ethanol or water; or aprotic solvents such as dimethylsulfoxide, dimethylformamide or hexamethylphosphorotriamide. In an even more preferred embodiment, the solvent is ethanol or water; and the most preferred is a combination of water and ethanol.

Examples of acceptable bases used in the present method are those with alkali metals or alkaline earth metals such as sodium, potassium, calcium and magnesium, and those with organic bases including, but not limited to, amines. Preferred bases are alkali metal bases or alkaline earth metal bases. Even more preferred bases are alkaline metal carbonates, such as, for example, potassium carbonate or sodium carbonate.

In another preferred embodiment, the method of the present invention is carried out at temperatures of from between 0° C. and 150° C. More preferably, the reaction temperature is from between 50° C. and 100° C. and even more preferably the reaction temperature is from between 65° C. and 90° C. A most preferred temperature is around 80° C.

Another preferred embodiment of the present invention, as depicted in Scheme 2, relates to preparing an aromatic azide intermediate Ia by reacting an aromatic amine IV with a nitrate ion to form the corresponding diazonium salt V. The diazonium salt V is then treated with an azide ion to afford the desired aromatic azide Ia.

Scheme 2

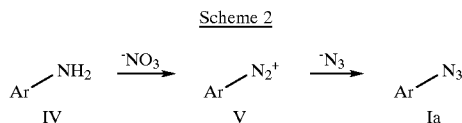

In Scheme 2:
Ar is aryl or heteroaryl optionally substituted with one, two or three groups independently selected from halogen, lower alkoxy, —C(O)-alkyl, hydroxy, amino, mono- or dialkylamino, —C(O)NH-alkyl, C(O)N-dialkyl, —NHC(O)-alkyl, alkenyl or alkynyl.

In yet another preferred embodiment, Scheme 3 shows a method of preparing alkyl azide intermediates Ib by $S_N2$ substitution of the corresponding halide VI using azide ion as the nucleophile.

Scheme 3

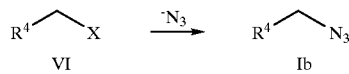

In Scheme 3:
X is a suitable leaving group, including but not limited to a halide, a mesylate or a tosylate;

$R^4$ is lower alkyl or cycloalkyl optionally substituted with one, two or three groups independently selected from lower alkoxy, —C(O)-alkyl, hydroxy, amino, mono- or dialkylamino, —C(O)NH-alkyl, C(O)N-dialkyl, —C(O)O-alkyl, —NHC(O)-alkyl, cyano, alkenyl or alkynyl, or $R^4$ is aryl, arylalkyl, heteroaryl or heteroarylalkyl wherein the ring portion of each is optionally substituted with one, two or three groups independently selected from halogen, lower alkoxy, —C(O)-alkyl, hydroxy, amino, mono- or dialkylamino, —C(O)NH-alkyl, C(O)N-dialkyl, —C(O)O-alkyl, —NHC(O)-alkyl, cyano, alkenyl or alkynyl.

Scheme 4 shows yet another preferred embodiment of the present invention, which relates to preparing β-hydroxy alkyl azide intermediates Ic by regioselective nucleophilic opening of epoxide VII in the presence of ammonium chloride.

Scheme 4

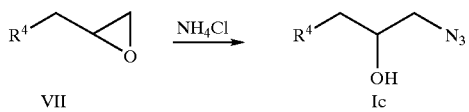

In Scheme 4:
$R^4$ is lower alkyl or cycloalkyl optionally substituted with one, two or three groups independently selected from lower alkoxy, —C(O)-alkyl, hydroxy, amino, mono- or dialkylamino, —C(O)NH-alkyl, C(O)N-dialkyl, —C(O)O-alkyl, —NHC(O)-alkyl, cyano, alkenyl or alkynyl, or $R^4$ is aryl, arylalkyl, heteroaryl or heteroarylalkyl wherein the ring portion of each is optionally substituted with one, two or three groups independently selected from halogen, lower alkoxy, —C(O)-alkyl, hydroxy, amino, mono- or dialkylamino, —C(O)NH-alkyl, C(O)N-dialkyl, —C(O)O-alkyl, —NHC(O)-alkyl, cyano, alkenyl or alkynyl.

Even more preferably, before treatment with the β-ketoester II, the β-hydroxy alkyl azide intermediate Ic is protected with conventional hydroxy-protecting groups known to those skilled in the art to survive the reaction conditions of the present invention. Preferred protecting groups are those that will form ethers. Most preferably, the hydroxy group is protected as the methyl ether.

The disclosures in this application of all articles and references, including patents, are incorporated herein by reference.

The invention is illustrated further by the following examples which are not to be construed as limiting the invention in scope or spirit to the specific procedures described in them.

The starting materials and various intermediates may be obtained from commercial sources, prepared from commercially available organic compounds, or prepared using well known synthetic methods.

Representative examples of methods for preparing intermediates of the invention are set forth below.

EXAMPLE 1

General Procedure for Large Scale Preparation of Aromatic Azides

An aniline (1 mol) is added to a solution of water (400 ml) and concentrated hydrochloric acid (225 ml). The resulting solution is stirred for 10 minutes before being cooled to 0° C. A solution of sodium nitrate (1.05 mol) in water (250 ml) is added in a dropwise manner. After being stirred for one hour, the mixture is filtered and the filtrate is cooled to 0° C. A solution of sodium azide (1.2 mol) in water (250 ml) is added in a dropwise manner (during the addition, the evolution of nitrogen gas is evident). After the addition is completed, the reaction is stirred for an additional 30 minutes. The reaction mixture is then extracted with ether (3×400 ml), and the combined organic extracts are washed with saturated sodium bicarbonate solution (400 ml) and then brine (400 ml), and dried over sodium sulfate. Removal of the volatiles in vacuo affords pure aryl azides in 80–90% yield.

1. 3,5-Difluorophenyl azide

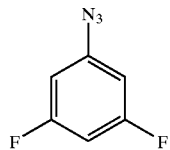

3,5-Difluoroaniline (64.5 g, 0.5 mol) is added to a solution of water (206 ml) and concentrated hydrochloric acid (116 ml). The resulting solution is stirred for 10 minutes and cooled to 0° C. A solution of sodium nitrate (37.4 g, 0.54 mol) in water (125 ml) is added in a dropwise manner. After being stirred for one hour, the mixture is filtered and the filtrate is cooled to 0° C. A solution of sodium azide (40.2 g, 0.62 mol) in water (125 ml) is added in a dropwise manner, and stirring is allowed to continue for 30 minutes. The reaction mixture is extracted with ether (3×250 ml), and the combined organic extracts are washed with saturated sodium bicarbonate solution (250 ml) and then brine (250 ml), and dried over sodium sulfate. Removal of the volatiles in vacuo affords pure title compound as a yellow liquid (70 g, 90%).

The following compounds are prepared essentially according to the same procedure:
 (a) 3-Fluoro-4-methylphenylazide (70 g); and
 (b) 4-Methoxyphenylazide (225 g).

Phenyl azide (54 g) is prepared according to the procedure found in Lindsay, R. O. et al., *Org. Synth. Coll. Vol.* 3, 710, incorporated herein by reference.

EXAMPLE 2

General Procedure for the Large Scale Preparation of Alkyl Azides

The alkyl azides are prepared essentially according to the procedure described in *Synthesis* 1997, 413, incorporated herein in its entirety.

A mixture of sodium azide (1 mol), dimethylsulfoxide (800 ml) and an alkyl bromide (0.5 mol) is stirred at room temperature (some substrates require slightly elevated temperatures) for 4 to 20 hours. The reaction mixture is poured into ice water and extracted with ether (3×400 ml). The combined organic extracts are washed with water (500 ml) and then brine (500 ml), and dried over sodium sulfate. Evaporation of the volatiles in vacuo affords the pure alkyl azides (85–95% yield).

1a. 2-(Azidomethyl)-tetrahydro-2H-pyran

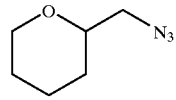

A mixture of sodium azide (65 g, 1 mol), dimethylsulfoxide (800 ml), and 2-(bromomethyl)-tetrahydro-2H-pyran (89.5 g, 0.5 mol) is stirred at 50° C. for 12 hours. The reaction mixture is allowed cool to room temperature and then slowly poured into ice water. The reaction is extracted with ether (3×400 ml). The combined organic extracts are washed with water (500 ml) and then brine (500 ml), and dried over sodium sulfate. Removal of the volatiles in vacuo affords the pure title compound (62 g, 88%) as a colorless oil.

1b. Benzyl azide

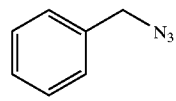

A mixture of sodium azide (76 g, 1.169 mol), dimethylsulfoxide (800 ml) and benzyl bromide (100 g, 0.584 mol) is stirred at room temperature for 5 hours. The reaction mixture is then slowly poured into ice water and extracted with ether (3×400 ml). The combined organic extracts are washed with water (500 ml), brine (500 ml) and dried over sodium sulfate. Removal of the volatiles in vacuo affords pure title compound (77 g, 99%) as a colorless oil.

The following compounds are prepared essentially according to the same procedure:
 (a) (1-Azidoethyl)benzene (20 hours at room temperature; 56 g);
 (b) Cyclopentylazide (20 hours at room temperature; 41 g);
 (c) 2-Azidomethyltetrahydrofuran (12 hours at 50° C.; 62 g);
 (d) Azidomethylcyclohexane (12 hours at 50° C.; 66 g); and
 (e) 3-Azidomethylpentane (2 hours at room temperature followed by 2 hours at 40° C.; 98 g).

EXAMPLE 3

General Procedure for the Large Scale Preparation of β-Methoxy Azides from Epoxides To a solution of the epoxide (0.75 mol) in a mixture of ethanol (300 ml) and water (300 ml) is added ammonium chloride (1.5 mol) followed by sodium azide (1.25 mol). The resulting solution is stirred gently at 50° C. for 12 hours before being allowed to cool. The ethanol is removed in vacuo. A solution of 6 M hydrochloric acid is added until the reaction mixture is pH 7. The mixture is then extracted with ethyl acetate (2×500 ml) and the organic extracts are washed with brine (500 ml) and dried over sodium sulfate. Evaporation of the volatiles in vacuo affords the β-hydroxy azide (70–80%).

The β-hydroxy azide (0.5 mol) and tetrabutylammonium hydrogen sulfate (0.005 mol) are sequentially added to a solution of methylene chloride (350 ml) and a 50% w/w solution of sodium hydroxide (60 ml). The resulting mixture is vigorously stirred for 30 minutes before being cooled to 0° C. Dimethylsulfate (0.6 mol) is then added in a dropwise manner with vigorous stirring over a period of one hour. The reaction is allowed to warm to room temperature and stirred until t.l.c analysis reveals that the reaction is complete (ca. 20 hours). Upon completion, concentrated ammonium hydroxide solution (10 ml) is added, and the reaction is allowed to stir for 45 minutes. The reaction is poured into water and extracted with methylene chloride (2×250 ml). The organic extracts are washed with water (3×250 ml—or until the washings are neutral) and dried over sodium sulfate. Evaporation of the volatiles gives the pure β-methoxy azide (>98% pure by gc. 90–95% yield). If desired, further purification can be carried out by passing the material through a pad of silica eluting with hexane/ethyl acetate (9:1).

The following compounds are prepared essentially according to the same procedure:

(a) (3-Azido-2-methoxypropyl)benzene (113 g);
(b) 1-Azido-2-methoxy-4-methylpentane (21 g); and
(c) 1-Azido-2-methoxycyclohexane (101 g).

EXAMPLE 4

General Procedure for the Synthesis of β-Ketoesters

The β-ketoesters of the present invention are prepared essentially according to the procedures described in Oikawa, Y. et al., *Org. Synth. Coll. Vol.* 7, 359, (1988); Oikawa, Y. et al., *J. Org. Chem.*, 43, 2087 (1978); and Capozzi, G., *J. Org. Chem.*, 58, 7932 (1993).

1. Methyl 3-oxo-4-phenylbutanoate

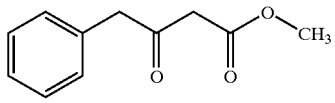

Pyridine (132 ml, 1.63 mol) is added to a cooled solution of recrystallized Meldrum's acid (95 g, 0.66 mol) in methylene chloride (200 ml) in a dropwise manner over 20 minutes under an inert atmosphere. To the resulting solution is added a solution of phenylacetyl chloride (100 g, 0.65 mol) in methylene chloride (200 ml) over a period of two hours. When the addition is complete, the orange cloudy reaction mixture is stirred for 1 hour at 0° C., and then for a further hour at room temperature. The reaction mixture is diluted with methylene chloride (100 ml), washed with 2M hydrochloric acid (250 ml) and brine (250 ml), and dried over sodium sulfate. Removal of the solvent in vacuo gives the crude acyl Meldrum's acid as an orange solid, which is used directly without any further purification.

The crude orange solid is refluxed in methanol (1 L) for 2.5 hours. The solvent is removed in vacuo, and the β-ketoester is purified by passing the crude material through silica gel eluting with pentane and ethyl acetate (9:1). The product (92.6 g, 80%) is obtained as a colorless oil.

EXAMPLE 5

Azide Opening of the Epoxide Followed by Protection 1. (1R,2R)-2-(Azadiazomvinyl)-1-methoxycyclohexane

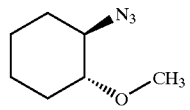

To a solution of cyclohexene oxide (150 g, 1.53 mol) in a mixture of ethanol (600 ml) and water (600 ml) is added ammonium chloride (168 g, 3.1 mol) followed by sodium azide (198 g, 3 mol). The resulting solution is stirred gently at 50° C. for 12 hours before being allowed to cool. The volatiles are removed in vacuo, and 6M hydrochloric acid (~120 ml) is added to bring the reaction to pH 7. The reaction is extracted with ethyl acetate (2×750 ml), and the organic extracts are washed with brine (750 ml) and dried over sodium sulfate. Removal of the solvent in vacuo affords 2-azido-cyclohexan-1-ol as a slightly yellow oil (171.8 g, 80%), which is used in the following step without further purification.

The azide (171.8 g, 1.22 mol) and tetrabutylammonium hydrogensulfate (4.2 g, 12.4 mmol) are sequentially added to a solution of methylene chloride (700 ml) and a 50% w/w aqueous solution of sodium hydroxide (129 g in 129 ml of water). The resulting mixture is vigorously stirred for 30 minutes before being cooled to 0° C. Dimethyl sulfate (186 g, 140 ml, 1.48 mol) is added in a dropwise manner to the vigorously stirred solution over a period of one hour, during which time a solid mass forms. This is broken up by addition of a further portion of methylene chloride (150 ml). The reaction mixture is then allowed to warm to room temperature and stirred for 20 hours. TLC analysis indicates a small amount of alcohol still remaining, and thus the reaction is allowed to proceed for an additional 12 hours at 50° C. After cooling to room temperature, the reaction is quenched by addition of concentrated ammonium hydroxide solution (100 ml) and allowed to stir for 45 minutes. The mixture is poured into water (500 ml) and extracted with methylene chloride (2×500 ml). The organic extracts are washed with water (3×500 ml) until the washings are neutral. The extracts are dried over sodium sulfate and the volatiles removed in vacuo. The crude product is passed through a plug of silica eluting with hexanes:ethyl acetate (9:1) to yield 1-azido-2-methoxycyclohexane (110 g, 58%) as a colorless oil.

EXAMPLE 6

General Procedure for the Synthesis of 1,2,3-Triazole Carboxylic Acids

The azide I (25 mmol), $K_2CO_3$ (10.5 g, 3 eq) and the keto-ester II (28 mmol) are combined in a 500 mL round bottomed flask. Aqueous ethanol (95%, 45 mL) is added followed by water (15 mL). The reaction is agitated at 80° C. for 16 hours, at which time the reaction mixture usually becomes homogeneous. The resulting dark solution is allowed to cool to room temperature and then extracted with 100 mL of EtOAc. The organic phase is discarded and the aqueous phase is cooled to 0° C. and neutralized with 1M HCl (approximately 150 mL). This results in the formation of a white precipitate. The precipitate is filtered off and washed with water. The final product is obtained by drying the precipitate over $P_2O_5$ under high vacuum.

Reaction yields typically range from 30%–95% and reactions are run on a scale up to about 100 g.

1. 1-[4-(Acetylamino)phenyl]-4-phenyl-1,2,3-triazole-5-carboxylic acid

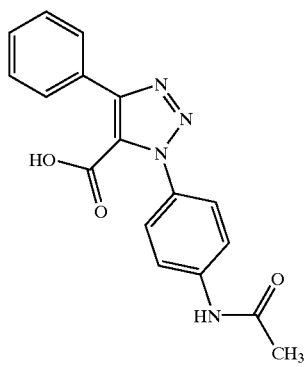

A suspension of 4-azidoacetanilide (4.4 g, 25 mmol), potassium carbonate (O.5 g, 76 mmol) and ethyl benzoylacetate (5.3 g, 4.75 ml, 27.6 mmol) in 95% ethanol (45 ml) and water (15 ml) is vigorously agitated at 80° C. for 16 hours. During this time, the reaction becomes homgeneous. The dark solution is allowed to cool to room temperature and extracted with ethyl acetate (100 ml). The organic extract is discarded, and the aqueous phase is cooled to 0° C. and neutralized with 1M hydrochloric acid (150 ml). The solid obtained is filtered and washed with cold water (100 ml) and methyl-t-butyl ether (100 ml) to give the triazole carboxylic acid as a colorless solid (12) (6.6 g, 82%).

Table 1 depicts other examples of 1,2,3-triazoles prepared essentially by the above-mentioned procedure.

TABLE 1

| Azide | Keto Ester | Scale (mmol) | Condition (base/ solvent/ temp.) | Product | Yield (mmol) (%) |
|---|---|---|---|---|---|
| ![N3-phenyl] | Methyl aceto acetate | 25 | K₂CO₃/EtOH and water/ 80° C. | 1 | 13.98 mmol; 56% |
| ![N3-3-fluoro-4-methylphenyl] | Methyl aceto acetate | 25 | K₂CO₃/EtOH and water/ 80° C. | 2 | 16.38 mmol; 66% |
| ![N3-3,5-difluorophenyl] | Methyl aceto acetate | 25 | K₂CO₃/EtOH and water/ 80° C. | 3 | 21.84 mmol; 87% |

TABLE 1-continued

| Azide | Keto Ester | Scale (mmol) | Condition (base/ solvent/ temp.) | Product | Yield (mmol) (%) |
|---|---|---|---|---|---|
| 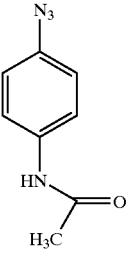 | Methyl aceto acetate | 25 | K₂CO₃/EtOH and water/ 80° C. | 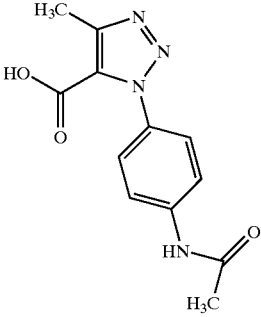<br>4 | 14.73 mmol; 59% |
| 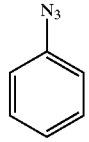 | Methyl propionyl acetate | 25 | K₂CO₃/EtOH and water/ 80° C. | 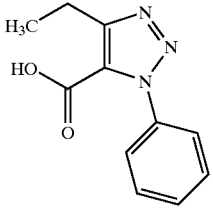<br>5 | 11.79 mmol; 47% |
| 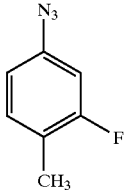 | Methyl propionyl acetate | 25 | K₂CO₃/EtOH and water/ 80° C. | 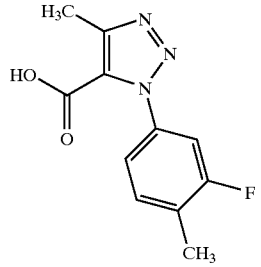<br>6 | 13.9 mmol; 56% |
| 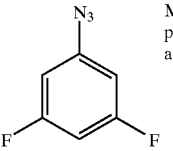 | Methyl propionyl acetate | 25 | K₂CO₃/EtOH and water/ 80° C. | 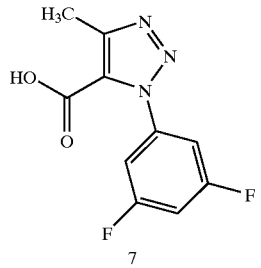<br>7 | 22.51 mmol; 90% |
| 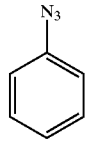 | Methyl 3-oxo-3-phenylpropanoate | 25 | K₂CO₃/EtOH and water/ 80° C. | 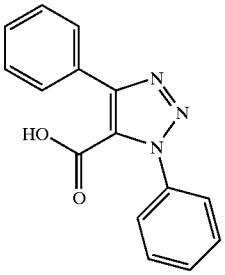<br>8 | 21.48 mmol; 86% |

TABLE 1-continued
| Azide | Keto Ester | Scale (mmol) | Condition (base/ solvent/ temp.) | Product | Yield (mmol) (%) |
|---|---|---|---|---|---|
| 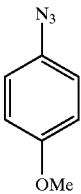 | Methyl 3-oxo-3-phenylpropanoate | 25 | K$_2$CO$_3$/EtOH and water/ 80° C. | 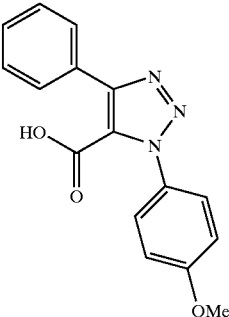<br>9 | 14.49 mmol; 58% |
| 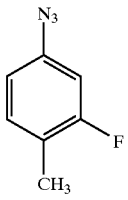 | Methyl 3-oxo-3-phenylpropanoate | 25 | K$_2$CO$_3$/EtOH and water/ 80° C. | 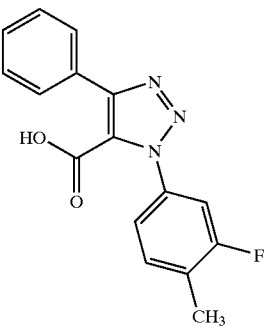<br>10 | 22.52 mmol; 90% |
| 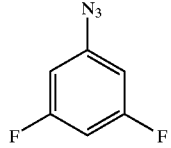 | Methyl 3-oxo-3-phenylpropanoate | 25 | K$_2$CO$_3$/EtOH and water/ 80° C. | 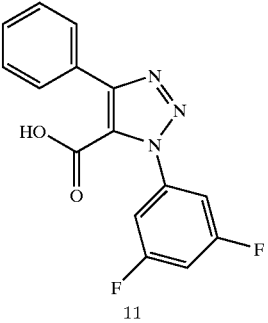<br>11 | 18.34 mmol; 73% |
| 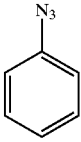 | Methyl 3-oxohexanoate | 25 | K$_2$CO$_3$/EtOH and water/ 80° C. | 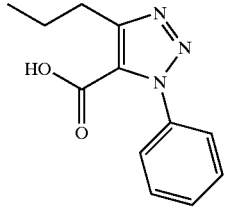<br>13 | 12.41 mmol; 50% |

TABLE 1-continued

| Azide | Keto Ester | Scale (mmol) | Condition (base/ solvent/ temp.) | Product | Yield (mmol) (%) |
|---|---|---|---|---|---|
| 3-fluoro-4-methylphenyl azide | Methyl 3-oxohexanoate | 25 | K₂CO₃/EtOH and water/ 80° C. | 14 | 19.23 mmol; 77% |
| 3,5-difluorophenyl azide | Methyl 3-oxohexanoate | 25 | K₂CO₃/EtOH and water/ 80° C. | 15 | 24.30 mmol; 97% |
| 4-acetamidophenyl azide | Methyl 3-oxohexanoate | 25 | K₂CO₃/EtOH and water/ 80° C. | 16 | 10.47 mmol; 42% |
| phenyl azide | Methyl 4-methoxy-3-oxobutanoate | 25 | K₂CO₃/EtOH and water/ 80° C. | 17 | 10.82 mmol; 43% |
| 4-methoxyphenyl azide | Methyl 4-methoxy-3-oxobutanoate | 25 | K₂CO₃/EtOH and water/ 80° C. | 18 | 12.06 mmol; 48% |

TABLE 1-continued

| Azide | Keto Ester | Scale (mmol) | Condition (base/ solvent/ temp.) | Product | Yield (mmol) (%) |
|---|---|---|---|---|---|
| 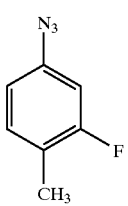 | Methyl 4-methoxy-3-oxobutanoate | 25 | K$_2$CO$_3$/EtOH and water/ 80° C. | 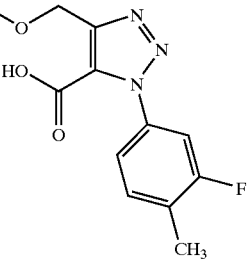<br>19 | 17.60 mmol; 70% |
| 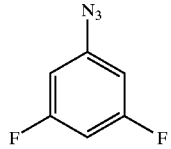 | Methyl 4-methoxy-3-oxobutanoate | 25 | K$_2$CO$_3$/EtOH and water/ 80° C. | 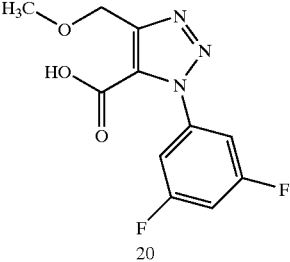<br>20 | 17.88 mmol; 72% |
| 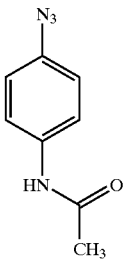 | Methyl 4-methoxy-3-oxobutanoate | 25 | K$_2$CO$_3$/EtOH and water/ 80° C. | 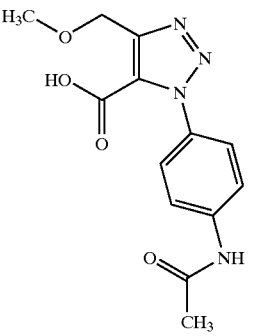<br>21 | 14.34 mmol; 57% |
| 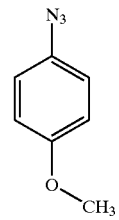 | Methyl 3-(2-fluorophenyl)-3-oxopropanoate | 25 | K$_2$CO$_3$/EtOH and water/ 80° C. | 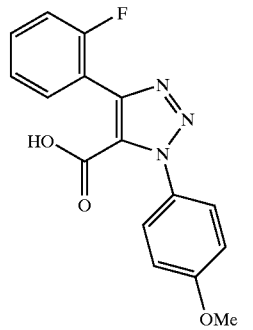<br>22 | 19.24 mmol; 77% |

TABLE 1-continued

| Azide | Keto Ester | Scale (mmol) | Condition (base/ solvent/ temp.) | Product | Yield (mmol) (%) |
|---|---|---|---|---|---|
| 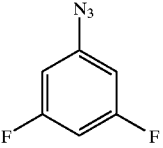 | Methyl 3-(2-fluorophenyl)-3-oxopropanoate | 25 | K$_2$CO$_3$/EtOH and water/ 80° C. | 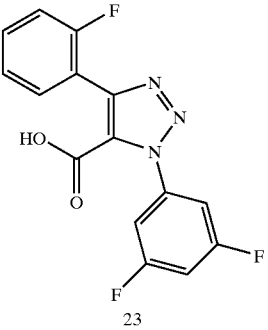<br>23 | 24.1 mmol; 96% |
| 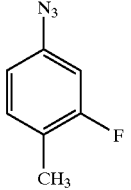 | Methyl 3-(2-fluorophenyl)-3-oxopropanoate | 25 | K$_2$CO$_3$/EtOH and water/ 80° C. | 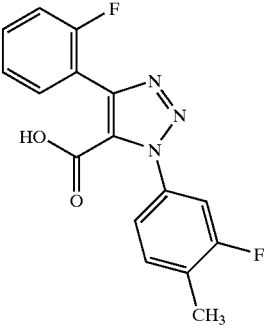<br>24 | 23.54 mmol; 94% |
| 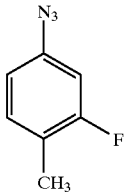 | Methyl 3-oxoheptanoate | 25 | K$_2$CO$_3$/EtOH and water/ 80° C. | 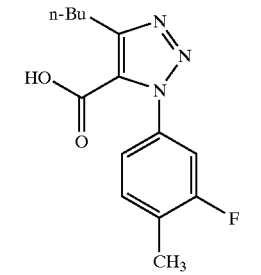<br>25 | 16.84 mmol 67% |
| 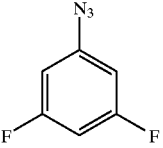 | Methyl 3-oxoheptanoate | 25 | K$_2$CO$_3$/EtOH and water/ 80° C. | 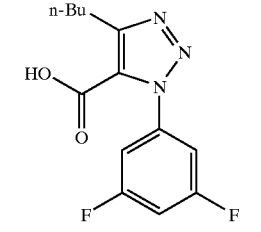<br>26 | 21.44 mmol; 86% |

The invention and manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as the invention, the following claims conclude this specification.

What is claimed is:

1. A method for preparing a 3H-[1,2,3]-triazole-4-carboxylic acid comprising treating an azide with a β-ketoester in the presence of a base.

2. The method of claim 1 wherein the 1,2,3-triazole carboxylic acid is

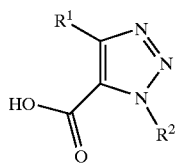

where
- $R^1$ and $R^2$ independently are lower alkyl or cycloalkyl optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, alkenyl or alkynyl, or
- $R^1$ and $R^2$ independently are aryl, arylalkyl, cycloalkylalkyl, heteroaryl or heteroarylalkyl wherein the ring portion of each is optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, alkenyl or alkynyl.

3. The method of claim 1 wherein the azide is treated with the β-ketoester in the presence of base at a temperature of from between 50° C. and 100° C.

4. The method of claim 3 wherein the temperature is about 80° C.

5. The method of claim 1 wherein the base is an alkali metal base, an alkali earth metal base or an organic base.

6. The method of claim 5 wherein the base is an alkali metal base or an alkali earth metal base.

7. The method of claim 6 wherein the base is potassium carbonate.

8. The method of claim 1 wherein the azide is treated with the β-ketoester in the presence of base in at least one suitable solvent.

9. The method of claim 8 wherein the at least one solvent is a protic solvent.

10. The method of claim 9 wherein the at least one protic solvent is a combination of ethanol and water.

11. A method of preparing a 1,2,3-triazole of the formula

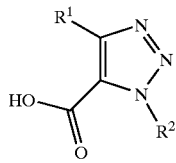

wherein $R^1$ and $R^2$ independently are lower alkyl or cycloalkyl optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, alkenyl or alkynyl, or $R^1$ and $R^2$ independently are aryl, arylalkyl, heteroaryl or heteroarylalkyl wherein the ring portion of each is optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, alkenyl or alkynyl;

the method comprising
treating an azide of the formula

with a β-ketoester of the formula

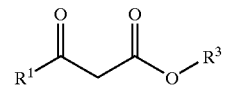

wherein $R^3$ is lower alkyl,
in the presence of a base.

12. The method according to claim 11 wherein $R^2$ is aryl or heteroaryl optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, alkenyl or alkynyl.

13. The method according to claim 12 wherein $R^2$ is phenyl optionally substituted with one, two or three groups independently selected from halogen, lower alkoxy, —C(O)-alkyl, hydroxy, amino, mono- or dialkylamino, mercapto, alkylthiol, —C(O)NH-alkyl, C(O)N-dialkyl, alkenyl or alkynyl.

* * * * *